US008108156B2

(12) United States Patent
Wang et al.

(10) Patent No.: US 8,108,156 B2
(45) Date of Patent: Jan. 31, 2012

(54) METHODS, PROGRAM PRODUCTS, AND SYSTEMS FOR ESTIMATING THE STRESS-STRAIN RELATIONSHIP OF A TOUGHENED STRUCTURAL ADHESIVE POLYMER

(75) Inventors: Kangping Wang, Troy, MI (US); Pei-Chung Wang, Shanghai (CN); John D. Fickes, Brighton, MI (US); Yih-Charng Deng, Rochester Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 574 days.

(21) Appl. No.: 12/266,059

(22) Filed: Nov. 6, 2008

(65) Prior Publication Data

US 2010/0114505 A1    May 6, 2010

(51) Int. Cl.
*G01L 1/00* (2006.01)
*G01N 3/00* (2006.01)

(52) U.S. Cl. ............ 702/42; 702/130; 702/182; 73/760; 73/789

(58) Field of Classification Search .................... 702/42; 73/760, 789, 795–796
See application file for complete search history.

(56) References Cited

U.S. PATENT DOCUMENTS

| | | | | |
|---|---|---|---|---|
| 2002/0065613 A1* | 5/2002 | Woods et al. | ................... | 702/42 |
| 2004/0254745 A1* | 12/2004 | Miyamoto et al. | ............. | 702/42 |
| 2005/0004779 A1* | 1/2005 | Ueda et al. | ................... | 702/182 |
| 2005/0065749 A1* | 3/2005 | Bernhardi et al. | ............ | 702/130 |

OTHER PUBLICATIONS

Ozel et al. Identification of Constitutive Material Model Parameters for High-Strain Rate Metal Cutting Conditions Using Evolutionary Computational Algorithms.*
Ozel et al. Identification of Constitutive Material Model Parameters for High-Strain Rate Metal Cutting Conditions Using Evolutionary Computational Algorithms, 2007, Materials and Manufacturing Processes, 22: pp. 659-667.*
Droste, A., "Crash stable adhesives in application and stimulation," 5. LS-DYNA Anwenderforum, Verbindungs-/Klebetechnik, Ulm 2006, pp. C-I-1-C-I-10.
DOW Automotive. Betamate 1484 Structural Adhesive Tech Data Sheet. Printed on Sep. 3, 2008.
Henkel Adhesive Technologies. Terokal 5087-02P, Nov. 2007, pp. 1-2.

* cited by examiner

*Primary Examiner* — Sujoy Kundu
*Assistant Examiner* — Michael Dalbo
(74) *Attorney, Agent, or Firm* — Ingrassia Fisher & Lorenz, P.C.

(57) ABSTRACT

Methods, program products, and computer systems for estimating a stress of a toughened structural adhesive polymer are provided. One method comprises selecting a strain, a strain rate, a temperature, or a combination thereof at which the stress is to be estimated. A value of a strain-hardening stress of the toughened structural adhesive polymer is determined, wherein the value of the strain-hardening stress is dependent on the temperature and the strain. A value of a non-strain-hardening stress of the toughened structural adhesive polymer is determined, wherein the value of the non-strain-hardening stress is dependent on the strain, the strain rate, and the temperature. The value of the strain-hardening stress is added to the value of the non-strain-hardening stress to obtain an estimated total stress.

18 Claims, 2 Drawing Sheets

METHODS, PROGRAM PRODUCTS, AND SYSTEMS FOR ESTIMATING THE STRESS-STRAIN RELATIONSHIP OF A TOUGHENED STRUCTURAL ADHESIVE POLYMER

FIELD OF THE INVENTION

The present invention generally relates to toughened structural adhesive polymers, and more particularly relates to methods, program products, and systems for estimating the stress-strain relationship of a toughened structural adhesive polymer.

BACKGROUND OF THE INVENTION

Recent trends toward economically fabricating vehicle structures while ensuring structural performance have led to the use of toughened structural adhesive polymers in the automotive industry. Structural adhesives are adhesives that generally exhibit good load-carrying capability, long-term durability, and resistance to heat, solvents, and fatigue. Toughened structural adhesive polymers are structural adhesives in which elastomeric particles are added or other means are used to increase the toughness of the polymer. Adhesive bonding of vehicle structures, such as, for example, metal vehicle structures, typically involves the use of structural adhesive polymers along with other means of joining the structures, such as by resistance spot welding or other assembly techniques, or riveting or other mechanical fastening techniques. The use of toughened structural adhesive polymers has been shown to offer better fatigue performance and greater flexibility in joining dissimilar materials when compared with, for example, resistance spot welding alone.

While a significant effort has been focused on developing toughened structural adhesive polymers, there is a need to understand the effects of various design variables on the performance of adhesively-bonded components. Furthermore, to facilitate the use of advanced high strength metals for lighter and stronger vehicles and vehicle joints, more cost-effective vehicle structure design guidelines and predictive capability of the dynamic performance of toughened adhesive-bonded joints are required. The development of such guidelines and predictive capability depends not only on an understanding of the impact characteristics of the metals but also the impact behavior of the toughened structural adhesives. While there is some understanding of the stress-strain relationship of toughened structural adhesives when subjected to impact strains at room temperature, information regarding the stress-strain relationship of toughened structural adhesive polymers when subjected to impact strains at various strain rates and at temperatures other than room temperature is still in high demand.

Accordingly, it is desirable to provide methods for estimating the stress of a toughened structural adhesive polymer when subjected to a selected strain at a selected strain rate and at a selected temperature. In addition, it is desirable to provide a program product for estimating the stress of a toughened structural adhesive polymer subjected to a selected strain at a selected strain rate and at a selected temperature. It also is desirable to provide a system for estimating the stress of a toughened structural adhesive polymer subjected to a selected strain at a selected strain rate and at a selected temperature. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for estimating a total stress of a toughened structural adhesive polymer is provided in accordance with an exemplary embodiment of the present invention. The method comprises the steps of selecting a strain, a strain rate, a temperature, or a combination thereof at which the stress is to be estimated. A value of a strain-hardening stress of the toughened structural adhesive polymer is determined, wherein the value of the strain-hardening stress is dependent on the temperature and the strain. A value of a non-strain-hardening stress of the toughened structural adhesive polymer is determined, wherein the value of the non-strain-hardening stress is dependent on the strain, the strain rate, and the temperature. The value of the strain-hardening stress is added to the value of the non-strain-hardening stress to obtain an estimated total stress.

A program product for estimating a stress of a toughened structural adhesive polymer at a selected strain, a selected strain rate, and a selected temperature is provided in accordance with an exemplary embodiment of the present invention. The program product comprises a program configured to at least facilitate: determining a value of a strain-hardening stress of the toughened structural adhesive polymer, wherein the value of the strain-hardening stress is dependent on the selected temperature and the selected strain; determining a value of a non-strain-hardening stress of the toughened structural adhesive polymer, wherein the value of the non-strain-hardening stress is dependent on the selected strain, the selected strain rate, and the selected temperature; and adding the value of the strain-hardening stress to the value of the non-strain-hardening stress to obtain an estimated total stress. A computer-readable signal-bearing media bears the program.

A system for estimating a total stress of a toughened structural adhesive polymer at a selected strain, a selected strain rate, and a selected temperature is provided in accordance with an exemplary embodiment of the present invention. The system comprises a processor configured to at least facilitate: receiving input signals derived from the selected strain, the selected strain rate, and the selected temperature; determining a value of a strain-hardening stress of the toughened structural adhesive polymer, wherein the value of the strain-hardening stress is dependent on the selected temperature and the selected strain; determining a value of a non-strain-hardening stress of the toughened structural adhesive polymer, wherein the value of the non-strain-hardening stress is dependent on the selected strain, the selected strain rate, and the selected temperature; and adding the value of the strain-hardening stress to the value of the non-strain-hardening stress to obtain an estimated total stress. An output device is coupled to the processor and is configured to at least facilitate displaying the total stress.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Methods for estimating the stress of a toughened structural adhesive polymer subjected to a selected strain at a selected strain rate and at a selected temperature, program products for estimating the stress of a toughened structural adhesive polymer subjected to a selected strain at a selected strain rate and at a selected temperature, and systems for estimating the stress of a toughened structural adhesive polymer subjected to a selected strain at a selected strain rate and at a selected temperature are provided herein. The methods, the program products, and the systems provide for the estimating of a stress-strain relationship of a toughened structural adhesive polymer at various conditions to which a vehicle may be subjected, including conditions indicative of an impact event. In this manner, the impact behavior of the structural adhesive polymer at various conditions can be predicted so that advanced vehicle materials and the joinder of such materials can be designed for optimized strength under a variety of environmental conditions. While the methods, program products, and systems are discussed in reference to use for vehicle applications, it will be appreciated that the methods, program products, and systems are no so limited and may be used to estimate the stress-strain relationship of any suitable toughened structural adhesive polymer used for any suitable application.

Figure 1:
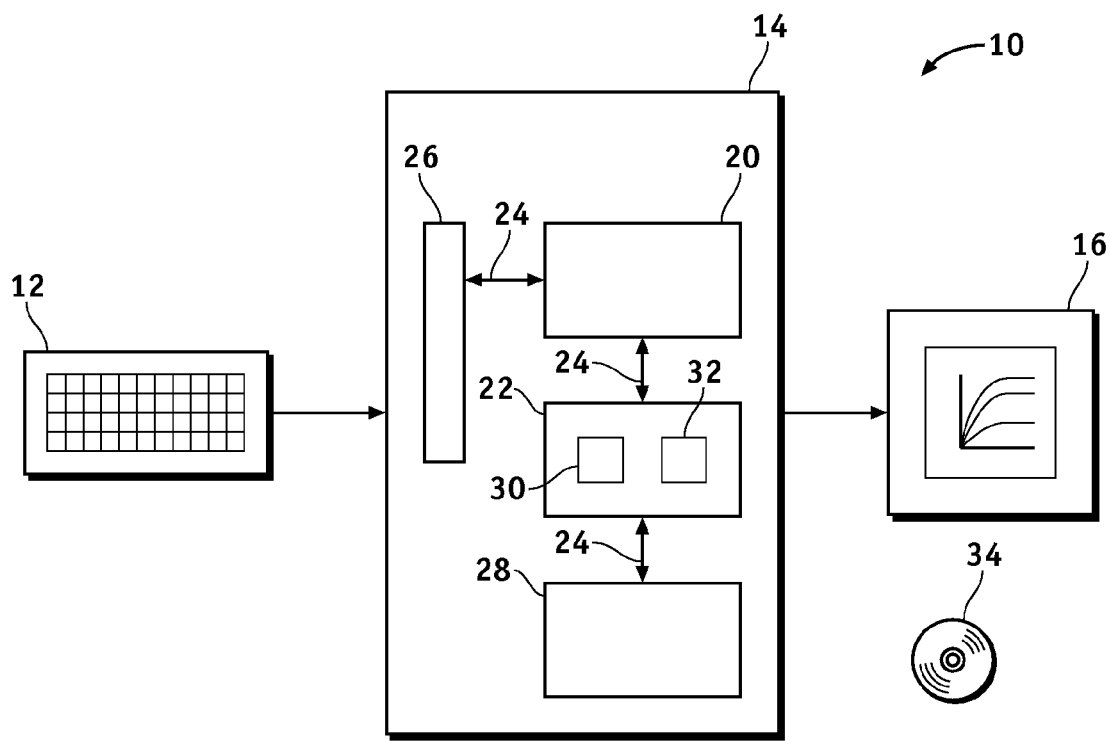
FIG. 1 is a block diagram of a computer system for estimating a stress of a toughened structural adhesive polymer at a selected strain, a selected strain rate, and a selected temperature, in accordance with an exemplary embodiment of the present invention.

FIG. 1 is a functional block diagram of a system 10 for estimating the stress-strain relationship of a toughened structural adhesive polymer, in accordance with an exemplary embodiment of the present invention. As used herein, the terms "structural adhesive polymer" and "structural adhesive" means any polymer that, when properly cured, possesses a relatively high modulus and high strength such that it can be used to join relatively rigid substrates, which may be similar or dissimilar substrates, so that a load-bearing joint is constructed. Structural adhesives are adhesives that generally exhibit good load-carrying capability, long-term durability, and resistance to heat, solvents, and fatigue. Examples of structural adhesive polymers include epoxy adhesives, polyurethane adhesives, modified acrylic adhesives, cyanoacrylate adhesives, and anaerobic adhesives. In a preferred embodiment, the structural adhesive polymer is a toughened structural adhesive polymer. Toughened structural adhesive polymers comprise polymers that have been toughened typically by the direct incorporation of finely dispersed elastomeric particles into the polymer, although toughened structural adhesive polymers toughened by other methods are contemplated herein. An example of a toughened structural adhesive polymer includes, but is not limited to, Terokal® 5087-02P available from Henkel Corporation of Germany.

As illustrated in FIG. 1, the system 10 comprises an input device 12, a computer module 14, and an output device 16. The input device 12 is configured to at least facilitate input from a user. In one exemplary embodiment of the present invention, the input comprises a strain rate at which a stress-strain relationship of the toughened structural adhesive polymer is to be estimated. In another exemplary embodiment, the input comprises a strain at which a stress-strain relationship of the toughened structural adhesive polymer is to be estimated. In yet another exemplary embodiment, the input comprises a temperature at which a stress-strain relationship of the toughened structural adhesive polymer is to be estimated. In a preferred embodiment, the input comprises a combination of a strain, a strain rate, and a temperature at which a stress-strain relationship of the toughened structural adhesive polymer is to be estimated. The input device 12 may comprise, for example, a keyboard or a touch panel, or any other suitable device suitable for use by a user or operator to provide the input to computer module 14.

The computer module 14 is coupled to the input device 12 and the output device 16. The computer module 14 is configured to at least facilitate estimating a stress-strain relationship of a toughened structural adhesive polymer based at least in part on a strain, a strain rate, and/or a temperature provided to the computer module 14 from the input device 12. The computer system 14 also is configured to provide instructions and data to the output device 16 for displaying output generated by the computer module.

The computer module 14 includes a processor 20, a memory 22, a computer bus 24, an interface 26, and a storage device 28. The processor 20 performs at least a portion of the computation and control functions of the computer system 14 and may comprise any type of processor or multiple processors, single integrated circuits such as a microprocessor, or any suitable number of integrated circuit devices and/or circuit boards working in cooperation to accomplish the functions of the processor 20. During operation, the processor 20 executes one or more programs 32 preferably stored within the memory 22 and, as such, controls the general operation of the computer module 14.

In a preferred embodiment, the processor 20 receives input signals from the input device 12 via interface 26, processes these signals utilizing stored data 30 stored in memory 22, generates output data that indicates an estimation of a stress-strain relationship of an toughened structural adhesive polymer based at least in part on these input signals, and provides the output data and instructions to the output device 16 for printing, displaying, or otherwise providing to a user of the system 10 the generated output data. In so doing, the processor 20 executes the program or programs 32 stored in memory 22.

The memory 22 stores the program or programs 32 that execute one or more embodiments of methods, such as a method 50 described in more detail below in reference to FIG. 2, and/or various steps thereof and/or other processes, such as those described elsewhere herein. In addition, as referenced above, the memory 22 also stores stored data 30 that may comprise strain values, strain rate values, and/or temperatures used to generate output data based on the input and based on the program or programs 32. The memory 22 can be any suitable type of memory such as, for example, dynamic random access memory (DRAM), various types of static random access memory (SRAM), and various types of non-volatile memory such as programmable read-only memory (PROM), erasable programmable read-only memory (EPROM), and flash memory. It should be understood that the memory 22 may be a single type of memory component or it may be composed of many different types of memory components. In addition, the memory 22 and the processor 20 may be distributed across several different computers that collectively comprise the computer module 14. For example, a portion of the memory 22 may reside on a computer within a particular apparatus, and another portion may reside on a remote computer.

The computer bus 24 serves to transmit programs, data, status, and other information or signals between the various components of the computer module 14. The computer bus 24 can be any suitable physical or logical means of connecting computer systems and components. This includes, but is not limited to, direct hard-wired connections, fiber optics, and infrared and wireless bus technologies.

The interface 26 allows communication to the computer module 14 from, for example, a computer system user or operator and/or another computer system, and can be implemented using any suitable method and apparatus. In a preferred embodiment, the interface 26 receives input from a user of the system 10 via the input device 12 and converts the input to input signals receivable by the processor 20.

The storage device 28 can be any suitable type of storage apparatus, including direct access storage devices such as hard disk drives, flash systems, floppy disk drives, and optical disk drives. In one exemplary embodiment, the storage device 28 is a program product from which memory 22 can receive a program 32 that executes one or more embodiments of the method 50 of FIG. 2 and/or steps thereof as described in greater detail below. In one exemplary embodiment, such a program product can be implemented as part of, inserted into, or otherwise coupled to the system 10. As shown in FIG. 1, the storage device 28 can comprise a disk drive device or other device that uses computer-readable signal-bearing media that store program or programs 32 and data. Examples of signal-bearing media suitable for use in performing method 50 include recordable media such as floppy disks, hard drives, memory cards, and optical disks (e.g., disk 34) and transmission media such as digital and analog communication links. As one exemplary embodiment, the computer module 14 also utilizes an Internet website, for example, for providing or maintaining data or performing operations thereon.

The output device 16 is coupled to computer module 14 and is configured to receive from computer module 14 output data indicative of a stress-strain relationship of a toughened structural adhesive polymer based, at least in part, on the input provided to input device 12 and on the stored data 30 and the programs 32 of memory 22. The output device 16 may be a display device such as, for example, a display screen as illustrated in FIG. 1 configured to display the output data on a screen, a printer configured to display the output data indicative of the stress-strain relationship in print form, or the like. The output data may be presented in the form of a graph, a table, text, or any other suitable means for providing the output data to a user.

It will be appreciated that, while the system 10 of FIG. 1 is described in the context of a fully functioning computer system, the system is capable of being distributed in a variety of forms and may be coupled to or may otherwise differ from the system 10 illustrated in FIG. 1, for example, by utilizing or otherwise being coupled to one or more remote computer systems and/or other control systems. In addition, method 50 described in more detail below may be performed by any number of types of computer systems using any number of computer-readable signal-bearing media.

Figure 2:
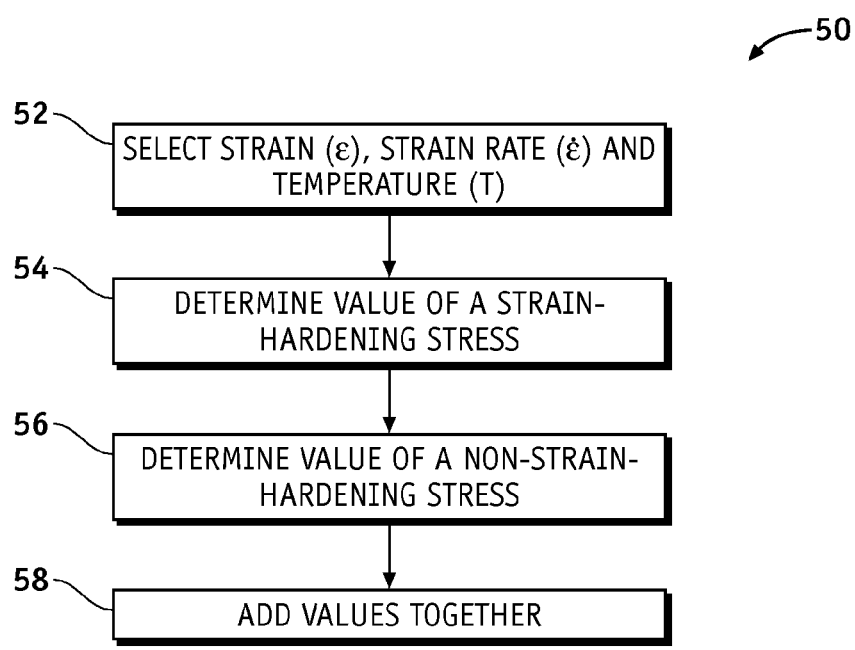
FIG. 2 is a flow chart of a method for estimating a stress of a toughened structural adhesive polymer at a selected strain, a selected strain rate, and a selected temperature, in accordance with an exemplary embodiment of the present invention.

FIG. 2 is a flowchart of method 50 for estimating the stress-strain relationship of a toughened structural adhesive polymer, in accordance with an exemplary embodiment of the present invention, which method can be performed using the system 10 of FIG. 1. In this regard, the stress-strain relationship is assessed by calculating an estimated "total stress" for a selected strain, a selected strain rate, and a selected temperature of interest. The "total stress" is the ratio of an applied load to an instantaneous area of the polymer supporting the load and can be estimated from the sum of the strain-hardening stress and the non-strain hardening stress exerted on the toughened structural adhesive polymer at the selected conditions. Accordingly, method 50 begins with the step of selecting a strain ($\epsilon$), a strain rate ($\dot{\epsilon}$) and a temperature (T) at which a stress-strain relationship of a selected toughened structural adhesive polymer is desired (step 52). The term "strain" as used herein is given its general dictionary meaning and is defined herein as a deformation of the adhesive polymer divided by its original length when subjected to an applied force. Accordingly, the term "strain rate" is defined as strain divided by the time duration the force is applied. The term "stress" as used herein is given its general dictionary meaning and is defined herein as the internal force per unit area associated with a strain. The strain ($\epsilon$) depends on the physical, mechanical, and chemical properties of the toughened structural adhesive polymer selected and can be obtained from experimental data or from look-up charts or tables.

In one exemplary embodiment, one, two, or all three of these parameters can be selected by the user of system 10 and provided to computer module 14 using input device 12, which parameter(s) is then transferred to processor 20 as input signals via interface 26. Alternatively, at least one of these parameters can be selected by the user of the system 10, with the other one or two parameters selected by system 10, such as by processor 20 from stored data 30 of memory 22. In another exemplary embodiment, one, two, or three of these parameters can be selected by another computer system coupled to system 10 and provided directly to processor 20, with any of the remaining parameters selected by processor 20 from stored data 30 of memory 22.

The temperature range to which method 50 applies is from about 23° C. to about 82° C. As noted above, there is some understanding of the stress-strain relationship of toughened structural adhesive polymers when subjected to impact strains at room temperature, which, for convenience is assigned a proximate value of 23° C. Temperatures as high as 82° C. represent approximately the maximum temperatures to which toughened structural adhesive polymers encountered in vehicles are subjected under extreme environmental conditions. At such high temperatures, certain toughened structural adhesive polymer could exhibit high deformation (i.e., high strain). It will be appreciated that the values of 23° C. and 82° C. are approximations of a room temperature and a high temperature of an extreme environmental condition at which the toughened structural adhesive polymer may be exposed. Method 50 contemplates any suitable deviation from these temperatures to temperatures that are indicative of room temperature and another higher temperature at which the adhesive polymer may be exposed, respectively. For example, room temperature may comprise a temperature in the range of from 15° C. to about 30° C.

The method 50 continues, in accordance with an exemplary embodiment of the present invention, with the steps of determining a value of a strain-hardening stress (step 54) and determining a value of a non-strain-hardening stress (56) that can be exerted on a toughened structural adhesive polymer when subjected to the selected strain at the selected strain rate and the selected temperature. These steps can be stored as programs 32 in memory 22 and can be executed, for example, by processor 20 of system 10. As used herein, the term "strain-hardening" means an increase in strength of the toughened structural adhesive polymer caused by visco-plastic (i.e., irreversible) deformation of the polymer at temperatures below its glass transition stage ($T_g$). "Strain-hardening stress" means the stress that can be exerted on a toughened structural adhesive polymer due to strain hardening. A non-strain-hardening stress means the stress that can be exerted on a toughened structural adhesive polymer, which lacks strain hardening under a given strain. Once a value of the strain-hardening stress and a value for the non-strain-hardening stress are determined, they are superimposed together by, for example, processor 20 of system 10, to obtain the total stress exerted on the toughened structural adhesive polymer when subjected to the selected strain and the selected temperature (step 58). Accordingly, the method 50 can be expressed by the following equation (1):

$$\sigma = \sigma_P + \sigma_H \tag{1}$$

where $\sigma_P$ represents the non-strain-hardening stress and $\sigma_H$ represents the strain-hardening stress.

Figure 3:
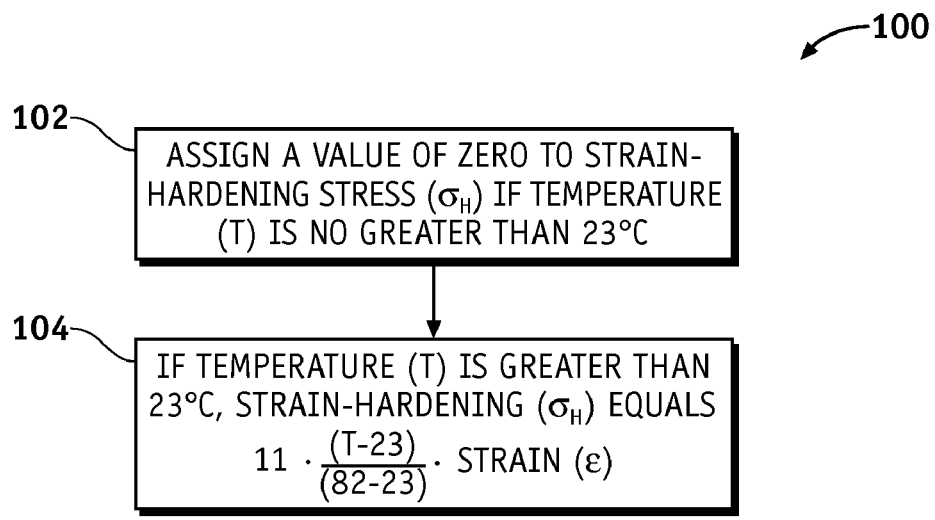
FIG. 3 is a flow chart of a method for determining a value of a strain-hardening stress as used in the method of FIG. 2, in accordance with an exemplary embodiment of the present invention.

A method 100 for determining a value of the strain-hardening stress ($\sigma_H$) that can be exerted on the toughened structural adhesive polymer when subjected to the selected strain at the selected temperature, in accordance with an exemplary embodiment of the present invention is illustrated in FIG. 3. The method 100 can be stored as a program or programs 32 in memory 22 and can be executed, for example, by processor 20 of system 10. The method 100 includes the step of assigning a value of zero to the strain-hardening stress if the temperature is no greater than 23° C. (step 102). Strain-hardening of the adhesive polymers contemplated herein typically is minimal and can be ignored at temperatures no greater than room temperature, which for convenience is assigned the value herein at 23° C. However, at temperatures greater than 23° C., stress caused by strain hardening can be considerable. Accordingly, for temperatures greater than 23° C., the strain-hardening stress ($\sigma_H$) is estimated by the following equation (2):

$$\sigma_H = 11 \times \frac{T(° C.) - 23° C.}{82° C. - 23° C.} \times \varepsilon, \tag{2}$$

where $\sigma_H$ is in units of megapascals (MPa) (step 104). Accordingly, equation (2) can be stored as a program or programs 32 in memory 22 of computer system 10 and can be executed by processor 10 using input signals that indicate the temperature at which the stress-strain relationship is desired. It will be appreciated that the temperatures 23° C. and 82° C. are approximations of a room temperature and a high temperature at which a vehicle in extreme conditions may be exposed, respectively; however, it will be appreciated that constants 23° C. and 82° C. of equation (2) may be replaced with any suitable approximation of room temperature and a higher environmental temperature, respectively. In one exemplary embodiment, constants 23° C. and 82° C. can deviate by from zero to about ±5° C. with equation (2) still providing a reliable estimate of the strain-hardening stress.

Figure 4:
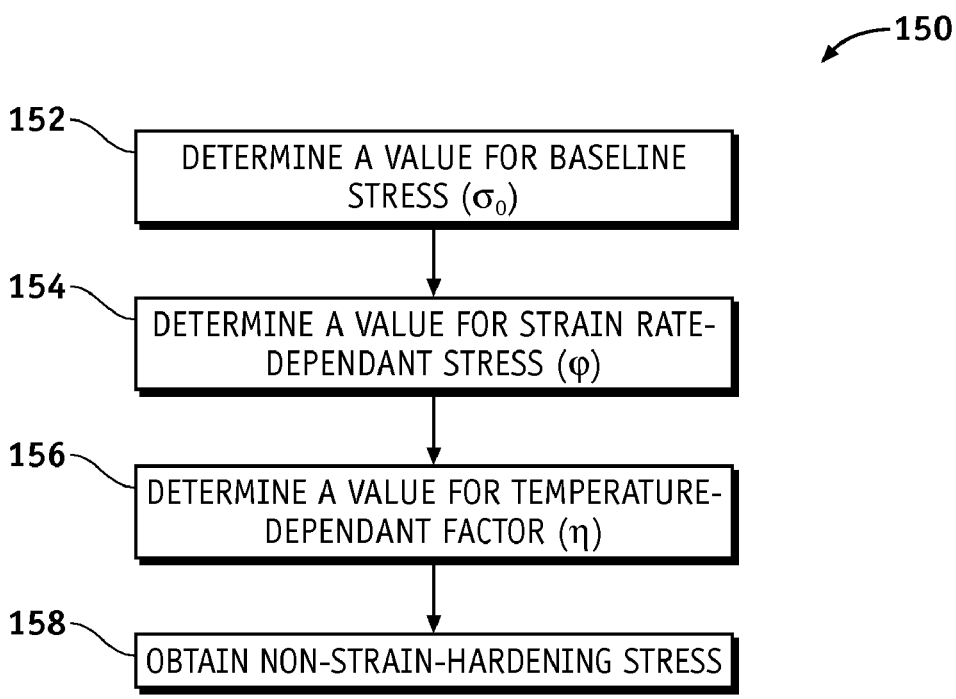
FIG. 4 is a flow chart of a method for determining a value of a non-strain-hardening stress as used in the method of FIG. 2, in accordance with an exemplary embodiment of the present invention.

In accordance with an exemplary embodiment of the present invention, a method 150 for determining a value of the non-strain-hardening stress ($\sigma_P$) of method 50 is illustrated in FIG. 4. Method 150 can be stored as a program or programs 32 in memory 22 and can be executed, for example, by processor 20 of system 10. The inventors have found that the non-strain-hardening stress ($\sigma_P$) can be reliably estimated by assessing three variables of the non-strain-hardening stress. In particular, the non-strain-hardening stress can be reliably estimated by assessing a baseline stress ($\sigma_0$), a strain-rate-dependent stress ($\phi$), and a temperature-dependent factor ($\eta$).

Accordingly, in accordance with one exemplary embodiment of the present invention, method 150 includes the step of determining a value for the baseline stress ($\sigma_0$) (step 152). The baseline stress represents that portion of the non-strain-hardening stress that is dependent only on strain and at which strain hardening can be ignored. It is known that, at a temperature of about −40° C. and a strain rate of about 0.001/second (sec.), strain-hardening is minimal and can be ignored. Accordingly, the inventors have found that these conditions can be used to assess a relationship for the baseline stress ($\sigma_0$), which relationship can be expressed by the following equation (3):

$$\sigma_0(\varepsilon) = 59.5 \times (1 - e^{-45 \cdot \varepsilon}) \tag{3}$$

wherein $\sigma_0(\varepsilon)$ is in units of megapascals (MPa). Accordingly, equation (3) can be stored as a program or programs 32 in memory 22 of computer system 10 and can be executed by processor 10 using input signals that indicate the strain at which the stress-strain relationship is desired. It will be appreciated that the constants 59.5 and −45 of equation (3) can deviate from these specified values by from about zero to about (±5%) with equation (3) still providing a usable estimate of the baseline stress ($\sigma_0$).

Method 150 continues in accordance with an exemplary embodiment with the determination of a value of the strain-rate-dependent stress ($\phi$) (step 154). The strain-rate dependent stress represents that portion of the non-strain-hardening stress that is dependent on the change of the strain rate as temperature changes. The inventors have found that the strain-rate-dependent stress ($\phi$) can be estimated by the following equation (4):

$$\varphi(\dot{\varepsilon}, T) = 1 + \frac{18.2}{100 - 1.07 \cdot T} \times lg(\dot{\varepsilon}/\dot{\varepsilon}_0), \tag{4}$$

wherein $\phi(\dot{\varepsilon}, T)$ is unitless and wherein $\dot{\varepsilon}_0$ is a reference strain rate that can be a minimal strain rate at which the stress-strain relationship is desired. An example of such a reference strain rate can be, for example, the condition set forth above for estimating the baseline stress, that is, a strain rate of 0.001/sec. Equation (4) can be stored as a program or programs 32 in memory 22 of system 10 and can be executed by processor 10 using input signals that indicate the strain rate and the temperature at which the stress-strain relationship is desired. It will be appreciated that the constants 1, 18.2, 100, and 1.07 of equation (4) can deviate by from about zero to about (±5%) with equation (4) still providing a usable estimate of the strain-rate-dependent stress ($\phi$).

In accordance with another exemplary embodiment of the present invention, method 150 also includes the step of determining a value of the temperature-dependent factor ($\eta$) (step 156). Temperature-dependent factor ($\eta$) represents that portion of the non-strain-hardening stress that is dependent on temperature alone at a reference strain rate, such as the reference strain rate used to estimate the strain-rate-dependent stress ($\phi$). The inventors have discovered that a reasonable estimate of the temperature-dependent factor can be obtained from the following equation (5):

$$\eta(T) = 1 - \left(\frac{T+40}{129}\right)^{0.75}, \quad (5)$$

wherein $\eta(T)$ is unitless. Equation (5) can be stored as a program or programs 32 in memory 22 of system 10 and can be executed by processor 10 using input signals that indicate the temperature at which the stress-strain relationship is desired. It will be appreciated that the constants 1, 40, 129, and 0.75 of equation (5) can deviate by from about zero to about (±5%) with equation (5) still providing a usable estimate of the temperature-dependent factor ($\eta$).

Once values are determined for the baseline stress ($\sigma_0$), the strain-rate-dependent stress ($\phi$), and the temperature-dependent factor ($\eta$), these values can be multiplied together according to the following equation (6) to obtain the non-strain-hardening stress ($\sigma_P$):

$$\sigma_P = \sigma_0(\epsilon) \times \phi(\dot{\epsilon}, T) \times \eta(T) \quad (6),$$

where the non-strain-hardening stress is in units of megapascals (step 158). Equation (6) can be stored as a program or programs 32 in memory 22 of system 10 and can be executed by processor 20 using the values calculated for the baseline stress ($\sigma_0$), the strain-rate-dependent stress ($\phi$), and the temperature-dependent factor ($\eta$).

Referring back to FIG. 2, in accordance with an exemplary embodiment of the present invention, after determination of a value for the strain-hardening stress $\sigma_H$ and a value of the non-strain-hardening stress up, the values can be added together according to equation (1) disclosed above to estimate the total stress of the toughened structural adhesive polymer when subjected to the selected strain ($\epsilon$) at the selected strain rate ($\dot{\epsilon}$) and the selected temperature (T) (step 58). Equation (1) can be stored as a program or programs 32 in memory 22 of system 10 and can be executed by processor 20 using the values calculated for the strain-hardening stress and the non-strain-hardening stress. Method 50 then can be repeated using equations (1) through (6) to estimate additional total stresses of the toughened structural adhesive polymer when subjected to additional selected strains at additional selected strain rates and temperatures to obtain a stress-strain relationship of the toughened structural adhesive polymer. While it will be appreciated that, although method 50 has been described with reference to equations (1) through (6) in that order, the steps of method 50 can be performed in any suitable order relative to each other. For example, while in FIG. 2, step 54 is illustrated as performed before step 56, it will be understood that the steps can be performed in the alternate order.

Accordingly, a method for estimating the stress of a toughened structural adhesive polymer subjected to a selected strain at a selected strain rate and at a selected temperature, a program product for estimating the stress of a toughened structural adhesive polymer subjected to a selected strain at a selected strain rate and at a selected temperature, and a system for estimating the stress of a toughened structural adhesive polymer subjected to a selected strain at a selected strain rate and at a selected temperature are provided herein. The method, the program product, and the system provide for estimating the stress-strain relationship of a toughened structural adhesive polymer at various conditions, including conditions indicative of an impact event. In this manner, the impact behavior of the toughened structural adhesive polymer at various conditions can be predicted so that advanced materials for use in vehicles and the joints of such materials can be designed for optimized strength under a variety of environmental conditions.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for estimating a total stress of a toughened structural adhesive polymer, the method comprising the steps of:
   receiving via an input device a strain, a strain rate, a temperature, or a combination thereof at which the total stress is to be estimated;
   accessing from a memory device computer instructions and causing the computer to perform:
   determining a value of a strain-hardening stress of the toughened structural adhesive polymer, wherein strain-hardening stress of the toughened structural adhesive polymer is assigned a value of zero if the temperature is no greater than about 23° C. and wherein the strain-hardening stress is determined using an equation:

$$\sigma_H = 11 \times \frac{T(° C.) - 23° C.}{82° C. - 23° C.} \times \epsilon,$$

if the temperature is greater than about 23° C., wherein $\sigma_H$ is in units of megapascals (MPa), wherein $\epsilon$ is the strain, T is the temperature, and wherein constants 11, 23° C., and 82° C. deviate by about zero to about ±5° C.;
   determining a value of a non-strain-hardening stress of the toughened structural adhesive polymer, wherein the value of the non-strain-hardening stress is dependent on the strain, the strain rate, and the temperature; and
   adding the value of the strain-hardening stress to the value of the non-strain-hardening stress to obtain an estimated total stress.

2. The method of claim 1, wherein the step of determining a value of the non-strain-hardening stress comprises the steps of:
   determining a value for a baseline stress ($\sigma_0$), a strain-rate-dependent stress ($\phi$), and a temperature-dependent factor ($\eta$); and
   multiplying the values of the baseline stress, the strain-rate-dependent stress and the temperature-dependent factor together.

3. The method of claim 2, wherein the step of determining a value for a baseline stress ($\sigma_0$), a strain-rate-dependent stress ($\phi$), and a temperature-dependent factor ($\eta$) comprises determining the value for the baseline stress using an equation:

$$\sigma_0(\epsilon) = 59.5 \times (1 - e^{-45 \cdot \epsilon}),$$

wherein $\sigma_0(\epsilon)$ is in units of megapascals and wherein constants 59.5, 1, and −45 deviate by from about zero to about ±5%.

4. The method of claim 2, wherein the step of determining a value for a baseline stress ($\sigma_0$), a strain-rate-dependent stress (φ), and a temperature-dependent factor (η) comprises determining the value for the strain-rate-dependent stress using an equation:

$$\varphi(\dot{\varepsilon}, T) = 1 + \frac{18.2}{100 - 1.07 \cdot T} \times lg(\dot{\varepsilon}/\dot{\varepsilon}_0),$$

wherein φ($\dot{\varepsilon}$, T) is unitless, wherein $\dot{\varepsilon}_0$ is a reference strain rate, and wherein constants 1, 18.2, 100, and 1.07 deviate by from about zero to about ±5%.

5. The method of claim 2, wherein the step of determining a value for a baseline stress ($\sigma_0$), a strain-rate-dependent stress (φ), and a temperature-dependent factor (η) comprises determining the value for the temperature-dependent factor using an equation:

$$\eta(T) = 1 - \left(\frac{T + 40}{129}\right)^{0.75},$$

wherein η(T) is unitless and wherein constants 1, 40, 129, and 0.75 can deviate by from about zero to about ±5%.

6. The method of claim 1, further comprising the step of selecting a second strain, a second strain rate, a second temperature, or a combination thereof and repeating the steps of determining and adding to obtain a second estimated total stress of the toughened structural adhesive polymer.

7. A non-transitory computer readable medium containing a computer program product comprising a computer program for estimating a total stress of a structural adhesive polymer at a selected strain, a selected strain rate, and a selected temperature, the:
computer program configured to at least facilitate:
determining a value of a strain-hardening stress of the toughened structural adhesive polymer, wherein the strain-hardening stress of the toughened structural adhesive polymer is assigned a value of zero if the temperature is no greater than about 23° C. and wherein the strain-hardening stress is determined using an equation:

$$\sigma_H = 11 \times \frac{T(° \text{C.}) - 23° \text{C.}}{82° \text{C.} - 23° \text{C.}} \times \varepsilon,$$

if the temperature is greater than about 23° C., wherein $\sigma_H$ is in units of megapascals (MPa),
wherein ε is the strain, and wherein constants 11, 23° C., and 82° C. deviate by about zero to about ±5° C.;
determining a value of a non-strain-hardening stress of the toughened structural adhesive polymer, wherein the value of the non-strain-hardening stress is dependent on the selected strain, the selected strain rate, and the selected temperature; and
adding the value of the strain-hardening stress to the value of the non-strain-hardening stress to obtain an estimated total stress.

8. The non-transitory computer readable medium of claim 7, wherein the computer program is configured to at least facilitate determining a value of the non-strain-hardening stress by:
determining a value for a baseline stress ($\sigma_0$), a strain-rate-dependent stress (φ), and a temperature-dependent factor (η); and
multiplying the values of the baseline stress, the strain-rate-dependent stress, and the temperature-dependent factor together.

9. The non-transitory computer readable medium of claim 8, wherein the computer program is configured to at least facilitate determining the value for the baseline stress using an equation:

$$\sigma_0(\varepsilon) = 59.5 \times (1 e^{-45 \cdot \varepsilon}),$$

wherein $\sigma_0(\varepsilon)$ is in units of megapascals and wherein constants 59.5, 1, and −45 deviate by from about zero to about ±5%.

10. The non-transitory computer readable medium of claim 8, wherein the computer program is configured to at least facilitate determining the value for the strain-rate-dependent stress using an equation:

$$\varphi(\dot{\varepsilon}, T) = 1 + \frac{18.2}{100 - 1.07 \cdot T} \times lg(\dot{\varepsilon}/\dot{\varepsilon}_0),$$

wherein ε($\dot{\varepsilon}$, T) is unitless, wherein $\dot{\varepsilon}_0$ is a reference strain rate, and wherein constants 1, 18.2, 100, and 1.07 deviate by from about zero to about ±5%.

11. The non-transitory computer readable medium of claim 8, wherein the computer program is configured to at least facilitate determining the value for the temperature-dependent factor using an equation:

$$\eta(T) = 1 - \left(\frac{T + 40}{129}\right)^{0.75},$$

wherein η(T) is unitless and wherein constants 1, 40, 129, and 0.75 deviate by from about zero to about ±5%.

12. A computer system for estimating a total stress of a toughened structural adhesive polymer at a selected strain, a selected strain rate, and a selected temperature, the computer system comprising:
a processor configured to at least facilitate:
receiving input signals derived from the selected strain, the selected strain rate, and the selected temperature;
determining a value of a strain-hardening stress of the toughened structural adhesive polymer, wherein the value of the strain-hardening stress is dependent on the selected temperature and the selected strain;
determining a value of a strain-hardening stress of the toughened structural adhesive polymer, wherein the strain-hardening stress of the toughened structural adhesive polymer is assigned a value of zero if the selected temperature is no greater than about 23° C. and wherein the strain-hardening stress is determined using an equation:

$$\sigma_H = 11 \times \frac{T(° \text{C.}) - 23° \text{C.}}{82° \text{C.} - 23° \text{C.}} \times \varepsilon,$$

if the selected temperature is greater than about 23° C., wherein $\sigma_H$ is in units of megapascals (MPa), wherein ε is the selected strain, and wherein constants 11, 23° C., and 82° C. deviate by about zero to about ±5° C.;
determining a value of a non-strain-hardening stress of the toughened structural adhesive polymer, wherein the value of the non-strain-hardening stress is dependent on the selected strain, the selected strain rate, and the selected temperature; and adding the value of the strain-hardening stress to the value of the non-strain-hardening stress to obtain an estimated total stress; and an output device coupled to the processor and configured to at least facilitate displaying the estimated total stress.

13. The system of claim 12, wherein the processor is configured to at least facilitate determining a value of the non-strain-hardening stress by:

determining a value for a baseline stress ($\sigma_0$), a strain-rate-dependent stress ($\phi$), and a temperature-dependent factor ($\eta$); and multiplying the values of the baseline stress, the strain-rate-dependent stress and the temperature-dependent factor together.

14. The system of claim 13, wherein the processor is configured to at least facilitate determining the value for the baseline stress using an equation:

$$\sigma_0(\epsilon) = 59.5 \times (1e^{-45\cdot}),$$

wherein $\sigma_0(\epsilon)$ is in units of megapascals and wherein constants 59.5, 1, and −45 deviate by from about zero to about ±5%.

15. The system of claim 13, wherein the processor is configured to at least facilitate determining the value for the strain-rate-dependent stress using an equation:

$$\varphi(\dot{\epsilon}, T) = 1 + \frac{18.2}{100 - 1.07 \cdot T} \times lg(\dot{\epsilon}/\dot{\epsilon}_0),$$

wherein $\phi(\dot{\epsilon}, T)$ is unitless, wherein $\dot{\epsilon}_0$ is a reference strain rate, and wherein constants 1, 18.2, 100, and 1.07 deviate by from about zero to about ±5%.

16. The system of claim 13, wherein the processor is configured to at least facilitate determining the value for the temperature-dependent factor using an equation:

$$\eta(T) = 1 - \left(\frac{T+40}{129}\right)^{0.75},$$

wherein $\eta(T)$ is unitless and wherein constants 1, 40, 129, and 0.75 can deviate by from about zero to about ±5%.

17. The system of claim 12, further comprising an input device coupled to the processor and configured to at least facilitate obtaining the selected strain, the selected strain rate, the selected temperature, or a combination thereof and transmit data indicative of the selected strain, the selected strain rate, the selected temperature, or a combination thereof to the processor.

18. The method of claim 1, further comprising sending to an output device the estimated total stress and causing the output device to display the estimated total stress on a display device.

* * * * *